United States Patent
Suwito et al.

(10) Patent No.: US 8,954,169 B2
(45) Date of Patent: Feb. 10, 2015

(54) SYSTEMS AND METHODS FOR LOADING A PRE-CURVED ELECTRODE ARRAY ONTO A STRAIGHTENING MEMBER

(75) Inventors: Wantjinarjo Suwito, Longmont, CO (US); Chuladatta Thenuwara, Castaic, CA (US); Christine Marr, Castaic, CA (US)

(73) Assignee: Advanced Bionics AG, Staefa (CH)

( * ) Notice: Subject to any disclaimer, the term of this patent is extended or adjusted under 35 U.S.C. 154(b) by 161 days.

(21) Appl. No.: 13/696,788

(22) PCT Filed: May 6, 2011

(86) PCT No.: PCT/US2011/035541
§ 371 (c)(1),
(2), (4) Date: Nov. 29, 2012

(87) PCT Pub. No.: WO2011/140454
PCT Pub. Date: Nov. 10, 2011

(65) Prior Publication Data
US 2013/0205562 A1 Aug. 15, 2013

Related U.S. Application Data

(60) Provisional application No. 61/332,488, filed on May 7, 2010.

(51) Int. Cl.
*A61N 1/04* (2006.01)
*B23P 19/00* (2006.01)
(Continued)

(52) U.S. Cl.
CPC .............. *B23P 19/00* (2013.01); *A61B 17/3468* (2013.01); *A61N 1/0541* (2013.01); *A61B 2017/0053* (2013.01); *A61B 2017/00787* (2013.01)
USPC .......................................................... 607/137

(58) Field of Classification Search
None
See application file for complete search history.

(56) References Cited

U.S. PATENT DOCUMENTS 4,819,647 A 4/1989 Byers et al.
4,898,183 A 2/1990 Kuzma
(Continued)

FOREIGN PATENT DOCUMENTS

EP 0109304 5/1984
EP 1233810 8/2002
(Continued)

OTHER PUBLICATIONS

International Search Report and Written Opinion received in International Application No. PCT/US2007/083428, dated May 20, 2008.
(Continued)

*Primary Examiner* — Brian T Gedeon
*Assistant Examiner* — Ankit Tejani
(74) *Attorney, Agent, or Firm* — ALG Intellectual Property, LLC

(57) ABSTRACT

Exemplary systems and methods for loading a pre-curved electrode array onto a straightening member are described herein. An exemplary system may include a loading tool including a housing and a slider member disposed at least partially within the housing. The slider member may be slidable from a first position to a second position and configured to move a pre-curved electrode array from a curved configuration to a straightened configuration as it slides from the first position to the second position. The exemplary system may also include a straightening member configured to be inserted into the pre-curved electrode array. Corresponding methods are also described.

20 Claims, 15 Drawing Sheets

(51) Int. Cl.
  *A61B 17/34* (2006.01)
  *A61N 1/05* (2006.01)
  *A61B 17/00* (2006.01)

(56) References Cited

U.S. PATENT DOCUMENTS

| | | | |
|---|---|---|---|
| 5,314,411 | A | 5/1994 | Bierman |
| 5,443,493 | A | 8/1995 | Byers et al. |
| 5,667,514 | A | 9/1997 | Heller |
| 6,070,105 | A | 5/2000 | Kuzma |
| 6,125,302 | A | 9/2000 | Kuzma |
| 6,129,753 | A | 10/2000 | Kuzma |
| 6,149,657 | A | 11/2000 | Kuzma |
| 6,195,586 | B1 | 2/2001 | Kuzma |
| 6,219,580 | B1 | 4/2001 | Faltys et al. |
| 6,272,382 | B1 | 8/2001 | Faltys et al. |
| 6,308,101 | B1 | 10/2001 | Faltys et al. |
| 6,421,569 | B1 | 7/2002 | Treaba et al. |
| 6,604,283 | B1 | 8/2003 | Kuzma |
| 6,968,238 | B1 | 11/2005 | Kuzma |
| 7,050,858 | B1 | 5/2006 | Kuzma et al. |
| 7,063,708 | B2 | 6/2006 | Gibson et al. |
| 7,269,461 | B2 | 9/2007 | Dadd et al. |
| 2002/0111634 | A1 | 8/2002 | Stoianovici et al. |
| 2003/0093139 | A1 | 5/2003 | Gibson et al. |
| 2004/0243177 | A1 | 12/2004 | Svehla et al. |
| 2005/0251237 | A1 | 11/2005 | Kuzma et al. |
| 2005/0267555 | A1 | 12/2005 | Marnfeldt et al. |
| 2006/0058861 | A1 | 3/2006 | Gibson et al. |
| 2006/0241723 | A1 | 10/2006 | Dadd et al. |
| 2007/0090735 | A1* | 4/2007 | Hashemi et al. ......... 312/334.46 |
| 2008/0004684 | A1 | 1/2008 | Dadd et al. |
| 2008/0021479 | A1* | 1/2008 | Penenberg ..................... 606/96 |
| 2008/0109011 | A1 | 5/2008 | Thenuwara et al. |
| 2008/0294174 | A1 | 11/2008 | Bardsley et al. |
| 2009/0187191 | A1* | 7/2009 | Carl et al. ....................... 606/80 |

FOREIGN PATENT DOCUMENTS

| | | |
|---|---|---|
| EP | 1341578 | 9/2003 |
| WO | WO-89/00870 | 2/1989 |
| WO | WO-93/24058 | 12/1993 |
| WO | WO-97/20530 | 6/1997 |
| WO | WO-00/71063 | 11/2000 |
| WO | WO-02/32498 | 4/2002 |
| WO | WO-0230507 | 4/2002 |
| WO | WO-02/074211 | 9/2002 |
| WO | WO-03070133 | 8/2003 |
| WO | WO-2004/012809 | 2/2004 |
| WO | WO-2008/057989 | 5/2008 |
| WO | WO 2008057989 A2 * | 5/2008 |

OTHER PUBLICATIONS

Non-Final Office Action received in U.S. Appl. No. 11/933,861, dated Apr. 14, 2010.
Non-Final Office Action received in U.S. Appl. No. 11/933,861, dated Oct. 1, 2010.
Final Office Action received in U.S. Appl. No. 11/933,861, dated Apr. 28, 2011.
International Search Report and Written Opinion received in International Application No. PCT/US2011/035541, dated Oct. 7, 2011.
International Search Report and Written Opinion received in International Application No. PCT/US2011/035539, dated Dec. 29, 2011.
Non-Final Office Action received in U.S. Appl. No. 13/696,789 dated Jan. 14, 2014.
Non-Final Office Action received in U.S. Appl. No. 12/485,427 dated Feb. 5, 2014.
"Surgeon's Practice Kit", Instructions for Use (Part No. Z60502), Cochlear Ltd (ABN 96 002 618 073), 14 Mars Road, Lane Cove NSW 2066, Australia, (2005).

* cited by examiner

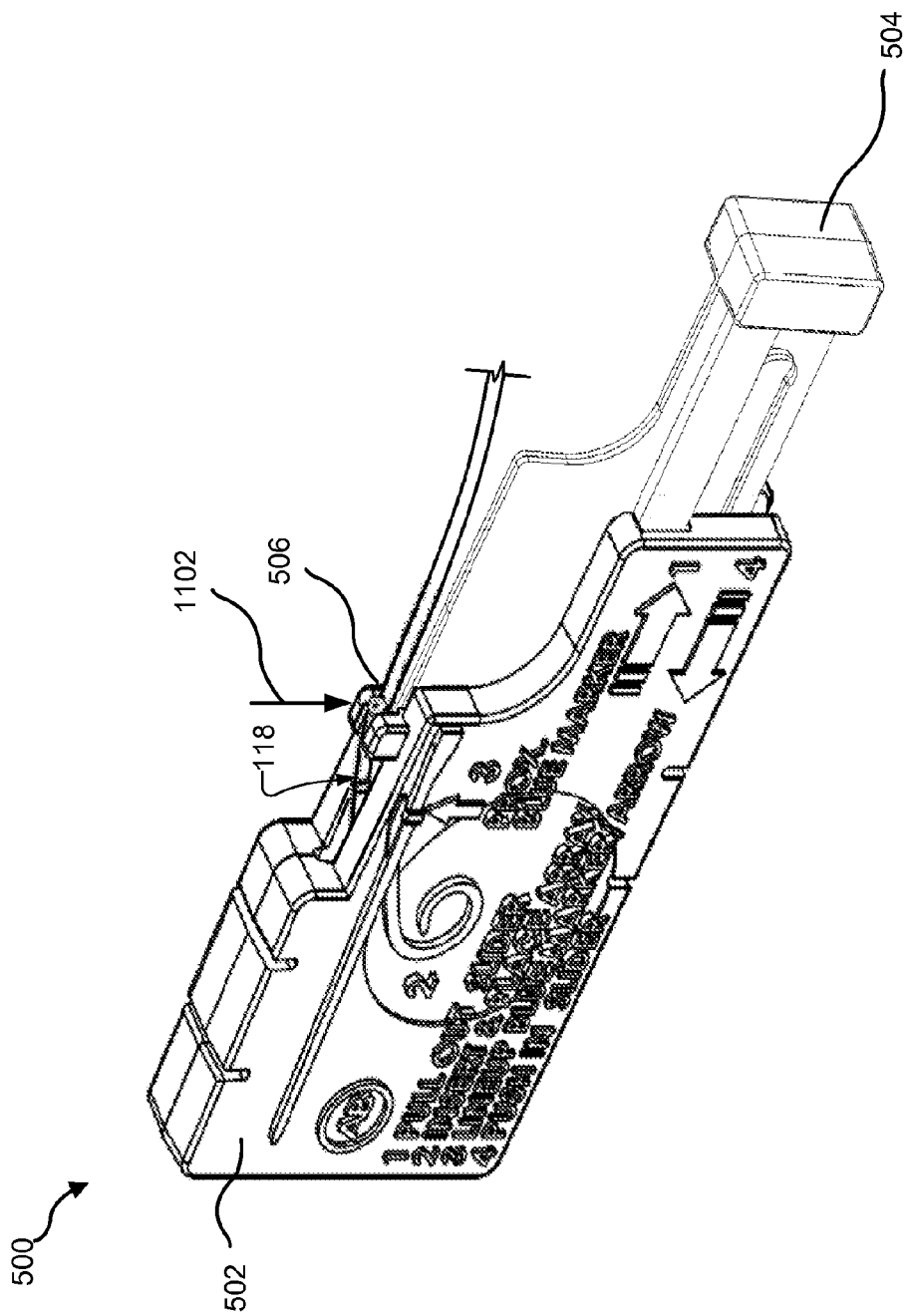

SYSTEMS AND METHODS FOR LOADING A PRE-CURVED ELECTRODE ARRAY ONTO A STRAIGHTENING MEMBER

RELATED APPLICATIONS

The present application claims priority to U.S. Provisional Patent Application No. 61/332,488 by Wantjinarjo Suwito et al., filed on May 7, 2010, and entitled "Systems and Methods for Loading a Pre-Curved Electrode Array onto a Straightening Member," the contents of which are hereby incorporated by reference in their entirety.

BACKGROUND

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an electrode array may be implanted in the cochlea. Electrodes included on the electrode array form stimulation channels through which electrical stimulation pulses may be applied directly to auditory nerves within the cochlea. An audio signal may therefore be presented to a patient by translating the audio signal into electrical stimulation pulses and applying the stimulation pulses directly to auditory nerves within the cochlea via one or more of the electrodes.

The electrode array is often implanted within the scala tympani, one of three parallel ducts that make up the spiral-shaped cochlea. Electrode arrays that are implanted in the scala tympani typically include several separately connected stimulating electrode contacts longitudinally disposed on a thin, elongate, and flexible carrier. Such an electrode array is pushed into the scala tympani duct via a surgical opening made in the cochlea wall at or near the round window at the basal end of the duct.

During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one electrode contact site tends to selectively activate those spiral ganglion cells and their auditory nerve fibers that are closest to that contact site.

Hence, it is often desirable for the electrode contacts to be positioned as close to the ganglion cells as possible and/or to any other location (e.g., a mid-scalar location) as may serve a particular application. To this end, various pre-curved electrode arrays have been developed that have spiral-shaped resilient carriers to better conform to the shape of the scala tympani and/or other auditory structures.

A pre-curved electrode array typically has to be loaded onto a straightening member, such as a stylet, before it can be inserted into the cochlea. It may also be necessary for a surgeon to reload the pre-curved electrode array onto the straightening member during a medical procedure. However, current methods of loading and reloading pre-curved electrode arrays onto straightening members are cumbersome and often result in damage to the pre-curved electrode arrays.

SUMMARY

An exemplary system for loading a pre-curved electrode array onto a straightening member may include a loading tool comprising a housing and a slider member disposed at least partially with the housing. The slider member may be slidable relative to the housing from a first position to a second position, wherein in the first position the housing and the slider member define a recess configured to receive the pre-curved electrode array in a curved configuration and wherein in the second position the housing and the slider member define a straightening channel configured to constrain the pre-curved electrode array in a straightened configuration. The slider member may be configured to move the pre-curved electrode array from the curved configuration to the straightened configuration as it slides from the first position to the second position. The exemplary system may also include a straightening member configured to be inserted into the pre-curved electrode array while the pre-curved electrode array is constrained in the straightened configuration and retain the pre-curved electrode array in the straightened configuration after the pre-curved electrode array is removed from the loading tool.

An exemplary method for loading a pre-curved electrode array onto a straightening member may include disposing the pre-curved electrode array at least partially into a loading tool. The loading tool may comprise a housing and a slider member disposed at least partially within the housing. The slider member may be slidable relative to the housing from a first position to a second position, wherein in the first position the housing and the slider member define a recess configured to receive the pre-curved electrode array in a curved configuration, wherein in the second position the housing and the slider member define a straightening channel configured to constrain the pre-curved electrode array in a straightened configuration. The slider member may be configured to engage the pre-curved electrode array to move the pre-curved electrode array from the curved configuration to the straightened configuration as it slides from the first position to the second position. The exemplary method may further include sliding the slider member from the first position to the second position to move the pre-curved electrode array from the curved configuration to the straightened configuration, inserting a straightening member at least partially into the pre-curved electrode array while the pre-curved electrode array is constrained in the straightened configuration to retain the pre-curved electrode array in the straightened configuration as the pre-curved electrode array is removed from the loading tool, and removing the pre-curved electrode array and inserted straightening member from the loading tool.

An exemplary tool for loading a pre-curved electrode array onto a straightening member may include a housing and a slider member disposed at least partially within the housing. The slider member may be slidable relative to the housing from a first position to a second position, wherein in the first position the housing and slider member define a recess configured to receive the pre-curved electrode array in a curved configuration, wherein in the second position the housing and the slider member define a straightening channel configured to constrain the pre-curved electrode array in a straightened configuration. The slider member may be configured to move the pre-curved electrode array from the curved configuration to the straightened configuration as it slides from the first position to the second position.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 11B illustrates a pre-curved electrode array being inserted into an exemplary loading tool according to principles described herein.

Throughout the drawings, identical reference numbers may designate similar, but not necessarily identical, elements.

DETAILED DESCRIPTION

Exemplary systems and methods for loading a pre-curved electrode array onto a straightening member are disclosed herein. The exemplary systems and methods described herein may allow a user (e.g., a surgeon) to more efficiently and easily load a pre-curved electrode array onto a straightening member (e.g., a stylet). As a result, the user may be able to load and/or reload a pre-curved electrode array onto a straightening member as needed during a medical procedure without significantly delaying the completion of the medical procedure or damaging the electrode array.

In some examples, a system according to principles described herein may include a loading tool comprising a housing and a slider member disposed at least partially within the housing. The slider member may be slidable relative to the housing from a first position to a second position. In the first position, the housing and the slider member define a recess configured to receive the pre-curved electrode array in a curved configuration. In the second position, the housing and the slider member define a straightening channel configured to constrain the pre-curved electrode array in a straightened configuration. As will be described in more detail below, the slider member may be configured to engage the pre-curved electrode array to move the pre-curved electrode array from the curved configuration to the straightened configuration as the slider member slides from the first position to the second position. The system may also include a straightening member configured to be inserted into the pre-curved electrode array while the pre-curved electrode array is constrained in the straightened configuration and retain the pre-curved electrode array in the straightened configuration after the pre-curved electrode array is removed from the loading tool.

Figure 1:
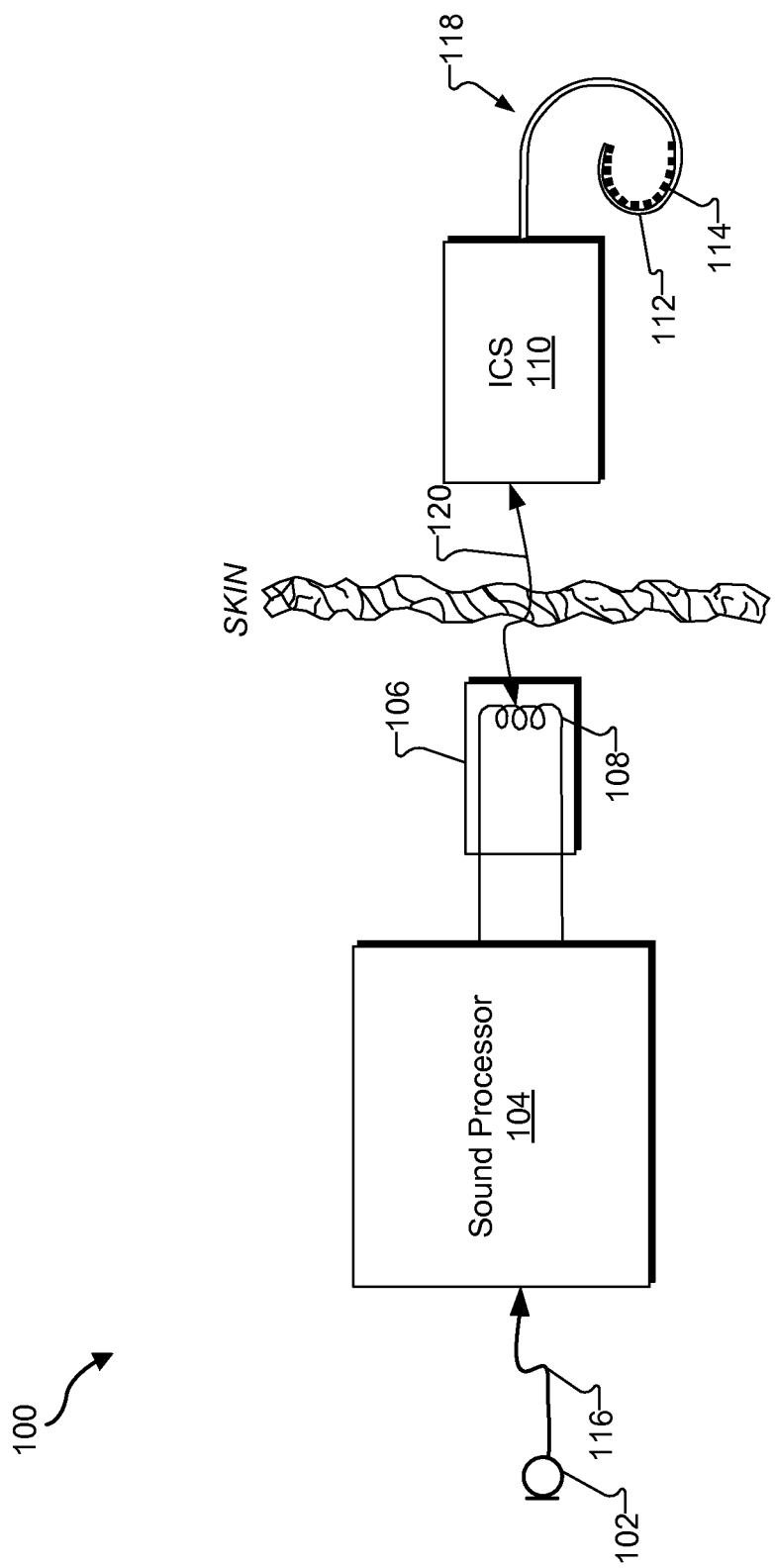
FIG. 1 illustrates an exemplary cochlear implant system according to principles described herein.

FIG. 1 illustrates an exemplary cochlear implant system 100. Cochlear implant system 100 may include a microphone 102, a sound processor 104, a headpiece 106 having a coil 108 disposed therein, an implantable cochlear stimulator ("ICS") 110, and a lead 118 having a pre-curved electrode array 112 (or simply "electrode array 112") comprising a plurality of electrodes 114. Additional or alternative components may be included within cochlear implant system 100 as may serve a particular application.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented within a behind-the-ear ("BTE") unit, a portable speech processor ("PSP"), and/or any other sound processing unit as may serve a particular application. Exemplary components of sound processor 104 will be described in more detail below.

Sound processor 104 may be configured to transcutaneously transmit one or more control parameters and/or one or more power signals to implantable cochlear stimulator 110 with coil 108 by way of communication link 120. These control parameters may be configured to specify one or more stimulation parameters, operating parameters, and/or any other parameter as may serve a particular application. Exemplary control parameters include, but are not limited to, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and back-end dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 120. It will be understood that data communication link 120 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 114 of electrode array 112 of lead 118.

To facilitate application of the electrical stimulation generated by implantable cochlear stimulator 110, electrode array 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Electrode array 112 may comprise any number of electrodes 114 (e.g., sixteen) as may serve a particular application.

Figure 2:
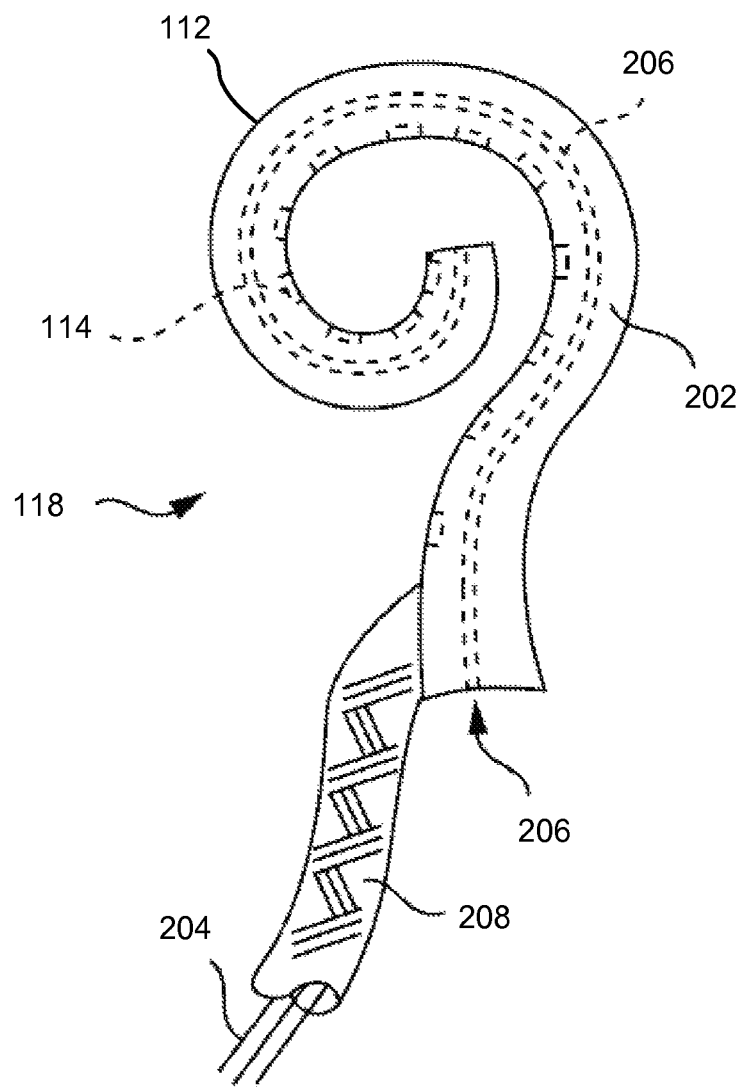
FIG. 2 illustrates an exemplary pre-curved electrode array according to principles described herein.

To facilitate proper positioning of electrodes 114, lead 118 is provided with a pre-curved electrode array 112 as shown in FIG. 2. The electrode array 112 may be substantially as shown and described in U.S. Pat. Nos. 4,819,647; 6,129,753; or 6,604,283, each of which is incorporated herein by reference in its respective entirety.

As shown in FIG. 2, electrode array 112 may have the same general curvature as that of a human cochlea. In some examples, electrode array 112 includes an array of electrodes 114 (also referred to as "electrode contacts 114") disposed on an elongate flexible carrier 202 and connected to corresponding wires 204, which may be insulated in some embodiments. Elongate flexible carrier 202 may be made out of any suitable material such as, but not limited to, silicone rubber or plastic, and has a hole or lumen 206 passing at least partially therethrough. In some examples, carrier 202 is constructed so as to have a built-in bias or memory force which forces carrier 202 to naturally assume the curved configuration shown in FIG. 2. In addition, the material of the carrier 202 may be configured to allow carrier 202 to be straightened when loaded on a straightening member. Hence, references made herein to "straightening a pre-curved electrode array" and/or "moving a pre-curved electrode array from a curved configuration to a straightened configuration" refer to a straightening of carrier 202. Once inserted within the duct of a cochlea, the memory force of carrier 202 forces carrier 202 to return to the desired curvature (e.g., as shown in FIG. 2).

As shown in FIG. 2, a proximal end of carrier 202 is coupled to a lead body 208 through which wires 204 continue and connect to implantable cochlear stimulator 110. Implantable cochlear stimulator 110 is thus able to make electrical connection with each of the electrodes 114 through one or more of wires 204. In some examples, the electrodes 114 of electrode array 112 are configured to be positioned along a medial electrode wall, i.e., the inside curve of carrier 202 such that they face the modiolus when implanted in the cochlea.

Figure 3:
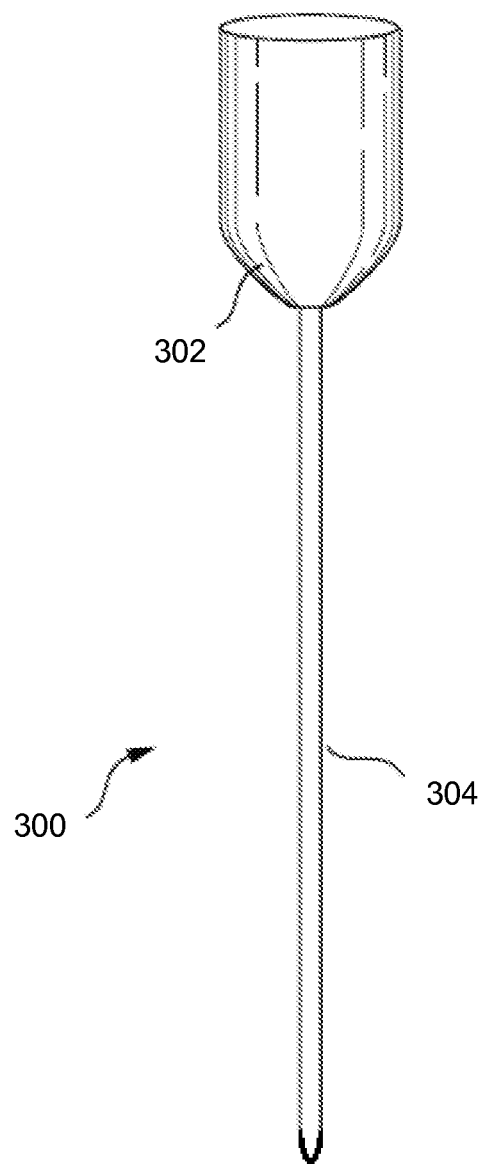
FIG. 3 is a perspective view of an exemplary straightening member that may be used to insert a pre-curved electrode array into a duct of the cochlea according to principles described herein.

As mentioned, pre-curved electrode array 112 may be loaded onto a straightening member before it can be implanted within a duct of the cochlea. FIG. 3 is a perspective view of an exemplary straightening member 300 that may be used in accordance with the systems and methods described herein. As shown in FIG. 3, straightening member 300 may include a handle member 302 coupled to a substantially straight member 304. Handle member 302 may be of a dimension to accommodate manual handling thereof and/or attachment of forceps or other tools thereto. Substantially straight member 304, as will be described in more detail below, may be configured to be at least partially inserted into a lumen of pre-curved electrode array 112. As shown, straightening member 300 may have a substantially rounded distal tip to facilitate insertion into an electrode array. In additional or alternative examples, the distal tip may have any other configuration (e.g., a bullet-shaped configuration or a substantially conical configuration) suitable for insertion into an electrode array without damaging the electrode array.

Straightening member 300 shown in FIG. 3 is a stand-alone stylet for illustrative purposes only. It will be recognized that straightening member 300 may alternatively be coupled to or a part of an insertion tool.

Straightening member 300 may be made out of any suitable material with sufficient stiffness so as to facilitate entry into the cochlea. For example, straightening member 300 may be made out of a metal, a metal alloy, a hard plastic, or any other suitable material.

Figure 4:
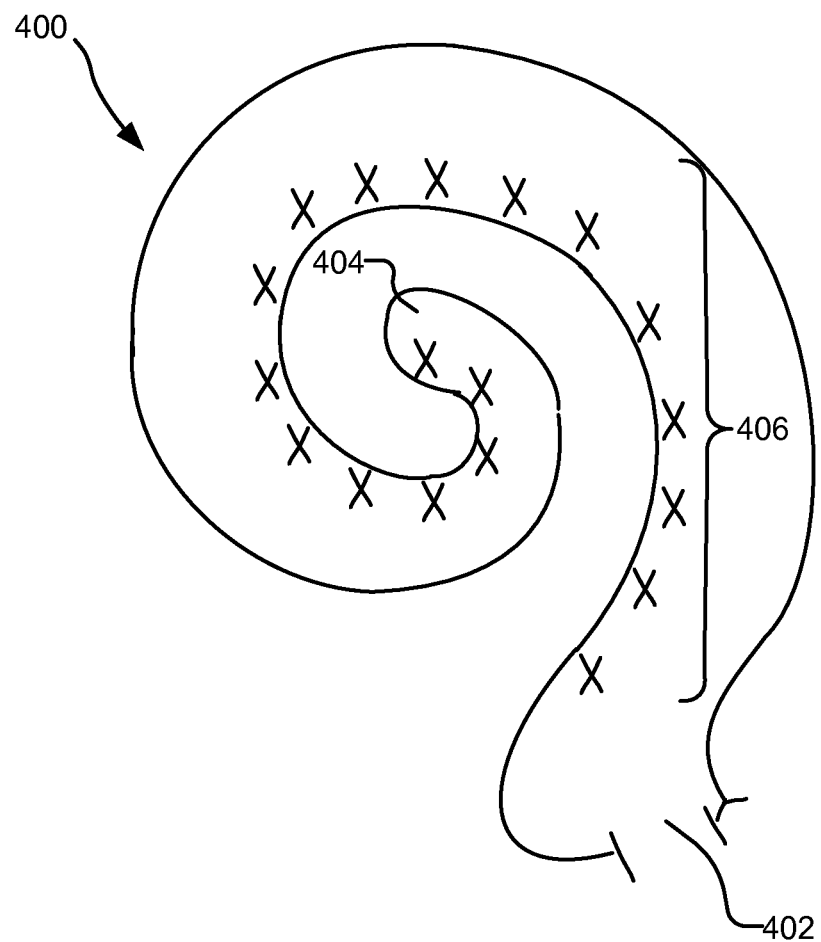
FIG. 4 illustrates a schematic structure of a human cochlea.

FIG. 4 illustrates a schematic structure of the human cochlea 400 into which electrode array 112 may be inserted. As shown in FIG. 4, the cochlea 400 is in the shape of a spiral beginning at a base 402 and ending at an apex 404. Within the cochlea 400 resides auditory nerve tissue 406, which is denoted by Xs in FIG. 4. The auditory nerve tissue 406 is organized within the cochlea 400 in a tonotopic manner. Low frequencies are encoded at the apex 404 of the cochlea 400 while high frequencies are encoded at the base 402. Hence, each location along the length of the cochlea 400 corresponds to a different perceived frequency. System 100 may therefore be configured to apply electrical stimulation to different locations within the cochlea 400 (e.g., different locations along the auditory nerve tissue 406) to provide a sensation of hearing.

Figure 5:
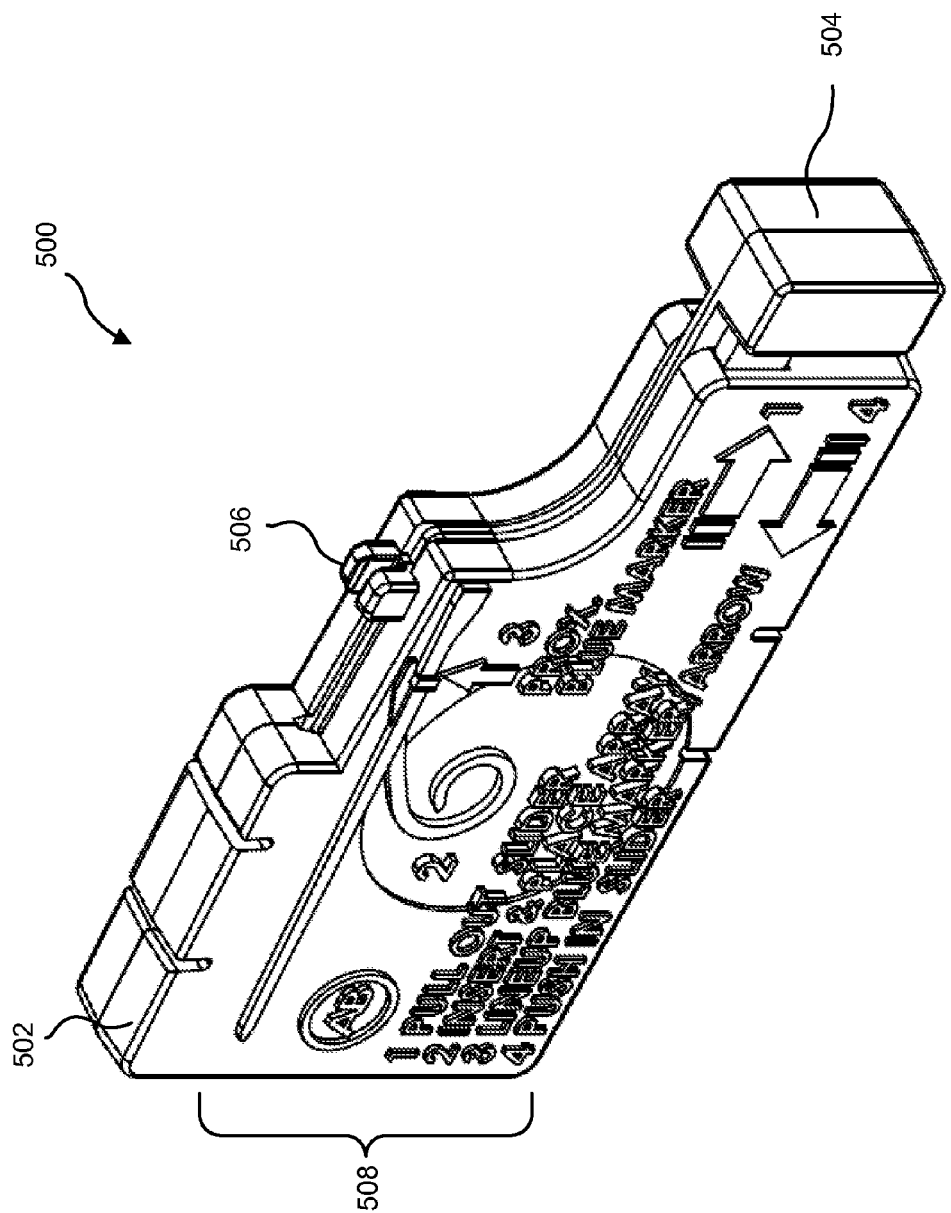
FIG. 5 is a perspective view of an exemplary loading tool according to principles described herein.

FIG. 5 is a perspective view of an exemplary loading tool 500 configured to load a pre-curved electrode array (e.g., pre-curved electrode array 112) onto a straightening member according to principles described herein. As shown in FIG. 5, loading tool 500 may include a housing 502 and a slider member 504 disposed at least partially within housing 502. In some examples, as will be explained in greater detail below, slider member 504 may be slidable relative to housing 502 from a first position to a second position. In the first position, housing 502 and slider member 504 define a recess configured to receive a pre-curved electrode array in a curved configuration. In the second position, housing 502 and slider member 504 define a straightening channel configured to constrain the pre-curved electrode array in a straightened configuration. As will be described in more detail below, slider member 504 may be configured to engage the pre-curved electrode array to move the pre-curved electrode array from a curved configuration to a straightened configuration as it moves from the first position to the second position.

As shown in FIG. 5, loading tool 500 may include a gripping element 506 configured to grip, stabilize, and/or hold any portion of a lead as slider member 504 moves from the first position to the second position. For example, gripping element 506 may include prongs extending up from housing 502 configured to grip opposite sides of a lead and prevent the electrode array from moving relative to housing 502 as the electrode array is straightened or as a straightening member is inserted into the electrode array. Additionally or alternatively, gripping element 506 may grip the lead in any other suitable manner (e.g., through a friction fit, an interference fit, a snap fit, etc.).

Housing 502 may be of any suitable shape and/or size as may serve a particular application. For example, housing 502 may be generally rectangular, as shown in FIG. 5. In some examples, housing 502 may be dimensioned to facilitate convenient handling thereof by a surgeon or other user. For example, an alternative shape of housing 502 than that shown in FIG. 5 may include a curved portion configured to rest on a user's index finger while the user moves slider member 504 from the first position to the second position.

Housing 502 may include instructions 508 disposed thereon to assist a user in utilizing loading tool 500. For example, as shown in FIG. 5, housing 502 may include written instructions (e.g., written steps) and graphical indicia (e.g., position markers, direction indicators, etc.) instructing a user on how to utilize loading tool 500. To illustrate, instructions 508 include written instructions that instruct a user to first "PULL OUT SLIDER," second "INSERT & PLACE ARRAY," third "LINEUP BLUE MARKER/ARROW," and fourth "PUSH IN SLIDER." In turn, the graphical indicia may correspond to the written instructions and include graphical objects (e.g., representing an electrode array in a straightened or curved configuration), direction indicators (e.g., arrows representing the directions to move slider member 504 during operation of loading tool 500), position markers (e.g., markers indicating where to line up a lead), and/or any other suitable graphical indicia. Instructions 508 are provided for exemplary purposes only. One will appreciate that instructions 508 may include any other written instructions, graphical indicia, and/or other symbols configured to provide instruction to a user on how to utilize loading tool 500. Additionally or alternatively, a lead configured to be utilized with loading tool 500 may include indicia (e.g., position markers) thereon corresponding to instructions 508 disposed on housing 502. In some examples, instructions 508 may be integrally formed with housing 502 (e.g., instructions 508 may include raised lettering and/or graphics molded onto housing 502).

Figure 6:
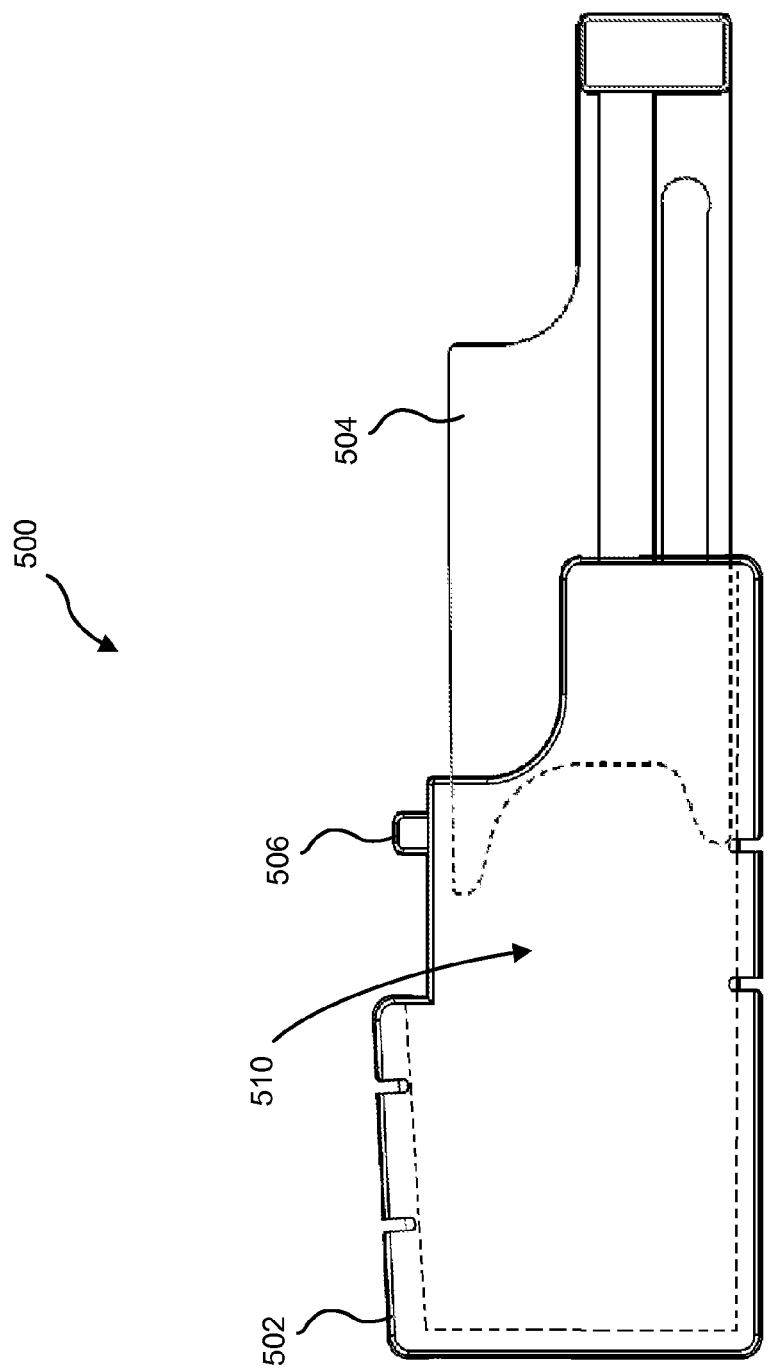
FIG. 6 illustrates the exemplary loading tool of FIG. 5 with an exemplary slider member in a first position according to principles described herein.

Reference is now made to FIG. 6, which illustrates a side view of loading tool 500 with slider member 504 in a first position. In FIG. 6, exemplary an interior surface of housing 502 and a portion of slider member 504 disposed within housing 502 are shown with dashed lines. As shown, when slider member 504 is in the first position, housing 502 and slider member 504 may define a recess 510. Recess 510 may be configured to receive a pre-curved electrode array in a curved configuration, which will be described and shown in more detail in FIGS. 11A and 11B. For example, a user may dispose a curved distal portion of a pre-curved electrode array into recess 510 and a portion of the lead proximal of the pre-curved electrode array into gripping element 506. In certain examples, the interior surfaces of housing 502 may assist in stabilizing or aligning the electrode array when disposed within recess 510. In this manner, the user may position the pre-curved electrode array for straightening using loading tool 500. Thereafter, the user may move slider member 504 from the first position to a second position in order to straighten the electrode array.

Figure 7:
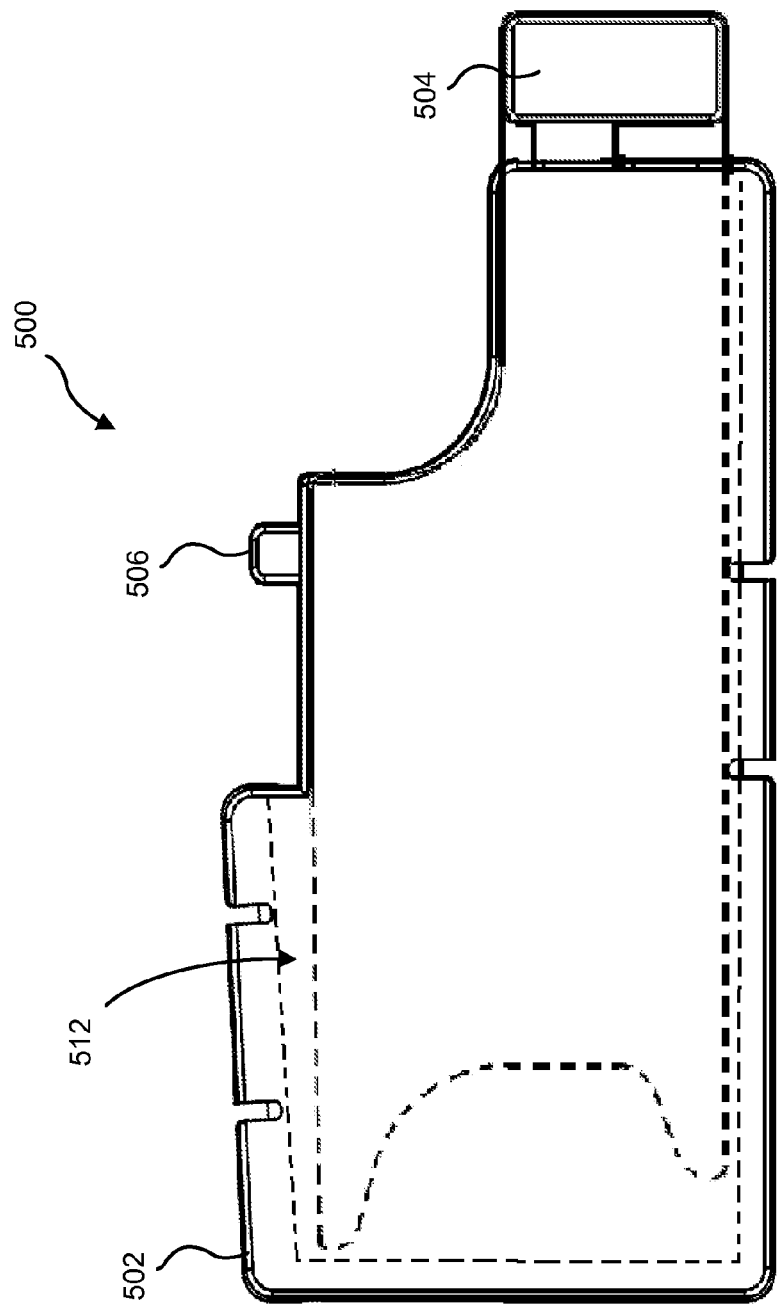
FIG. 7 illustrates the exemplary loading tool of FIG. 5 with an exemplary slider member in a second position according to principles described herein.

For example, FIG. 7 illustrates loading tool 500 with slider member 504 in a second position. As shown, with slider member 504 in the second position, housing 502 and slider member 504 define a straightening channel 512. Straightening channel 512 may be configured to constrain a pre-curved electrode array in a straightened configuration. For example, sliding slider member 504 from the first position shown in FIG. 6 to the second position shown in FIG. 7 may move a pre-curved electrode array from a curved configuration in recess 510 to a straightened configuration within straightening channel 512. In certain examples, slider member 504 may engage the pre-curved electrode array to move the pre-curved electrode array from the curved configuration to the straightened configuration as slider member slides from the first position to the second position. As a result, loading tool 500 may straighten the pre-curved electrode array so that a straightening member may be subsequently inserted into the pre-curved electrode array. Once the straightening member has been inserted into the straightened electrode array, the electrode array may be removed from loading tool 500 and inserted into the cochlea.

As mentioned above, straightening channel 512 may be configured to constrain an electrode array in a straightened configuration. Straightening channel 512 may be defined by one or more surfaces of housing 502 and slider member 504. In some examples, straightening channel 512 may have a size and shape that corresponds to the size and shape of a straightened electrode array. For example, straightening channel 512 may have a tapered configuration corresponding to an electrode array that tapers from a larger proximal end to a smaller distal end. In further examples, straightening channel 512 may have any size, shape, and/or configuration suitable for a particular application.

Figure 8:
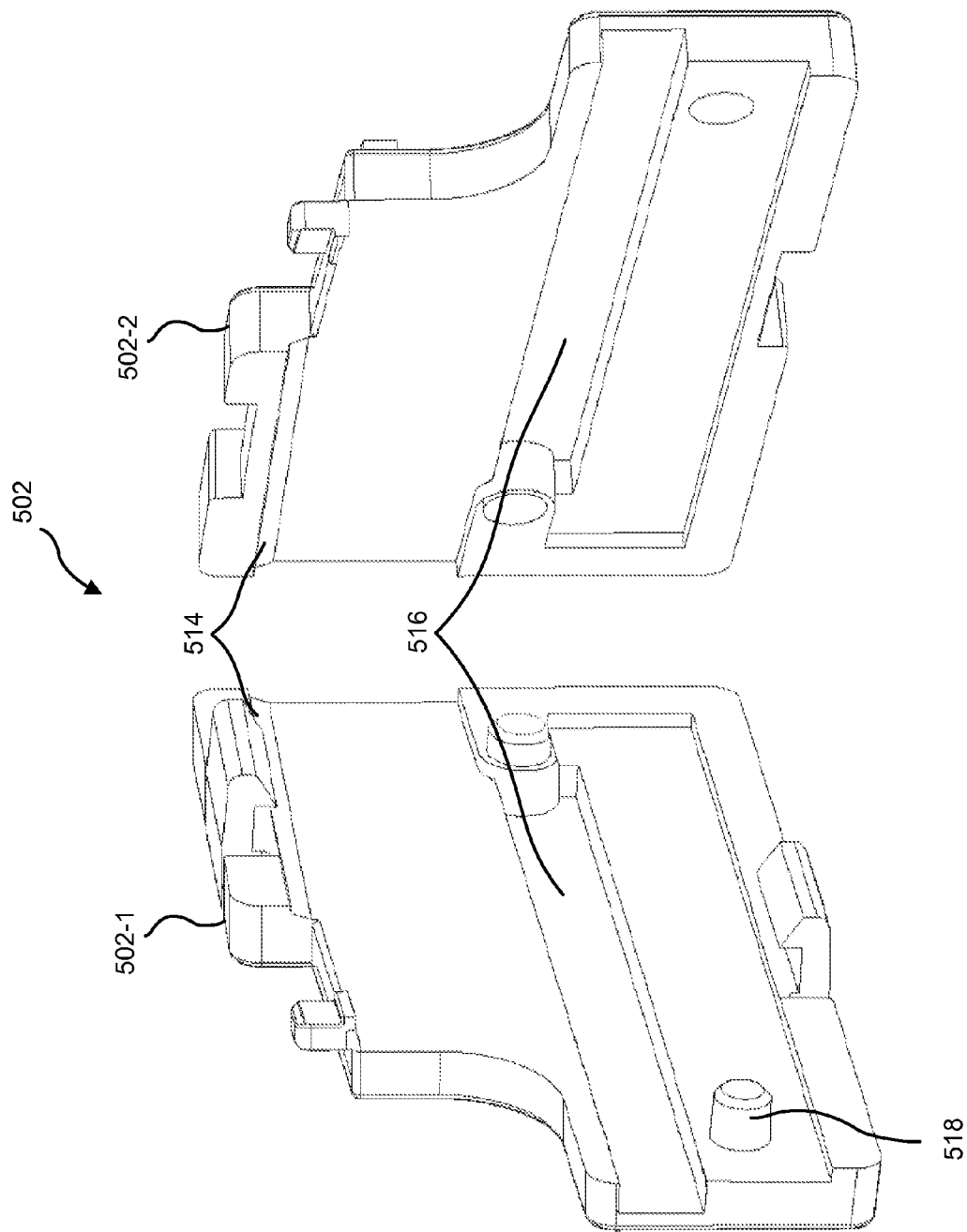
FIG. 8 illustrates an exploded view of an exemplary housing of the loading tool of FIG. 5 according to principles described herein.

Reference is now made to FIG. 8, which illustrates an exploded view of housing 502. As shown, housing 502 may include a first side member 502-1 and a second side member 502-2 configured to be coupled together. In certain examples, first side member 502-1 and second side member 502-2 may be configured to clip together. In further examples, one will appreciate that first side member 502-1 and second side member 502-2 may couple together in any other suitable manner (e.g., by way of a snap fit, a friction fit, an interference fit, etc.).

As shown in FIG. 8, first side member 502-1 and second side member 502-2 may each define one or more surfaces of straightening channel 512. In certain examples, first side member 502-1 and the second side member 502-2 may have inwardly angled surfaces 514 (or simply "angled surfaces 514") defining at least a portion of straightening channel 512 and configured to properly align an electrode array within straightening channel 512. For example, as slider member 504 moves an electrode array into straightening channel 512, angled surfaces 514 may engage the sides of the electrode array to ensure proper alignment for subsequent insertion of a straightening member into the electrode array.

In some examples, first side member 502-1 and second side member 502-2 may include one or more grooves 516 extending along a length thereof and configured to interact with one or more features of slider member 504 to guide slider member 504 as it slides from a first position to a second position. Additionally or alternatively, housing 502 may include a guide pin 518 extending from first side member 502-1 and/or second side member 502-2 and configured to interact with one or more features of slider member 504 to guide slider member 504 as it slides from a first position to a second position.

Figure 9A:
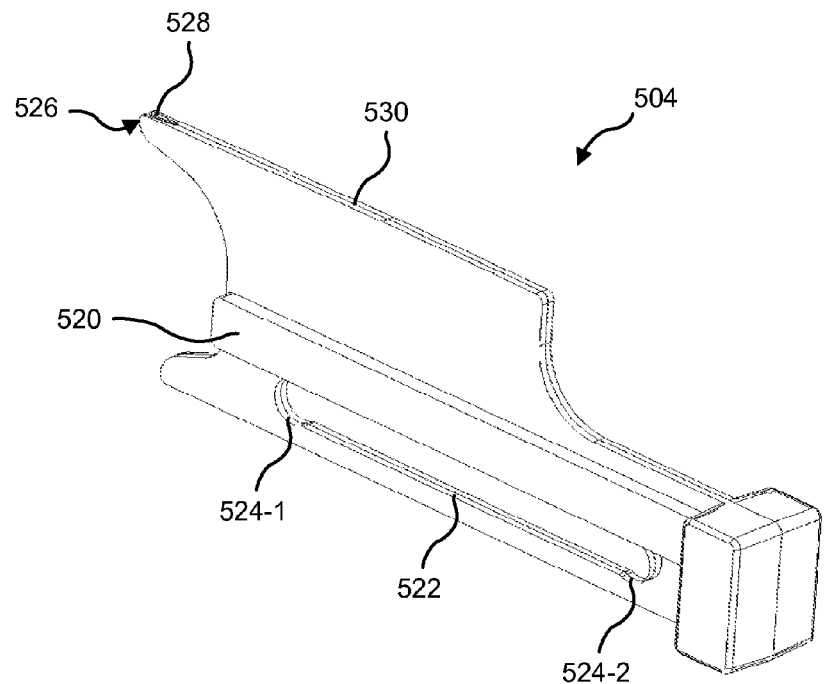
FIG. 9A is a perspective side view of an exemplary slider member of the loading tool of FIG. 5 according to principles described herein.

For example, as shown in FIG. 9A, which illustrates a perspective side view of slider member 504, slider member 504 may include one or more rails 520 extending along the length thereof and configured to interact with grooves 516 of housing 502 to guide the sliding of slider member 504 relative to housing 502. In certain examples, the size and shape of rails 520 may correspond to the size and shape of grooves 516. Additionally or alternatively, slider member 504 may include a guide channel 522 extending along a length thereof and configured to interact with guide pin 518 of housing 502 to guide slider member 504 as it slides relative to housing 502. For example, guide pin 518 may extend into or through guide channel 522 to guide slider member 504 as it slides from a first position to a second position. Guide pin 518 may interact with guide channel 522 to prevent slider member 504 from sliding beyond the first position or the second position or from becoming misaligned with housing 502.

Guide channel 522 may include a first indent 524-1 configured to receive guide pin 518 when slider member 504 is in the first position. In some examples, first indent 524-1 may be configured to resist movement of guide pin 518 away from first indent 524-1 and thereby resist movement by slider member 504 from the first position. Additionally or alternatively, guide channel 522 may include a second indent 524-2 configured to receive guide pin 518 when slider member 504 is in the second position. In some examples, second indent 524-2 may be configured to resist movement of guide pin 518 away from second indent 524-2 and thereby resist movement by slider member 504 from the second position. The resistance created by the interaction between guide pin 518 and first indent 524-1 and between guide pin 518 and second indent 524-2 may prevent inadvertent sliding of slider member 504 from the first position and second position, respectively. In certain examples, however, a user may apply a force sufficient to overcome this resistance in order to move slider member 504 between the first position and the second position.

Figure 9B:
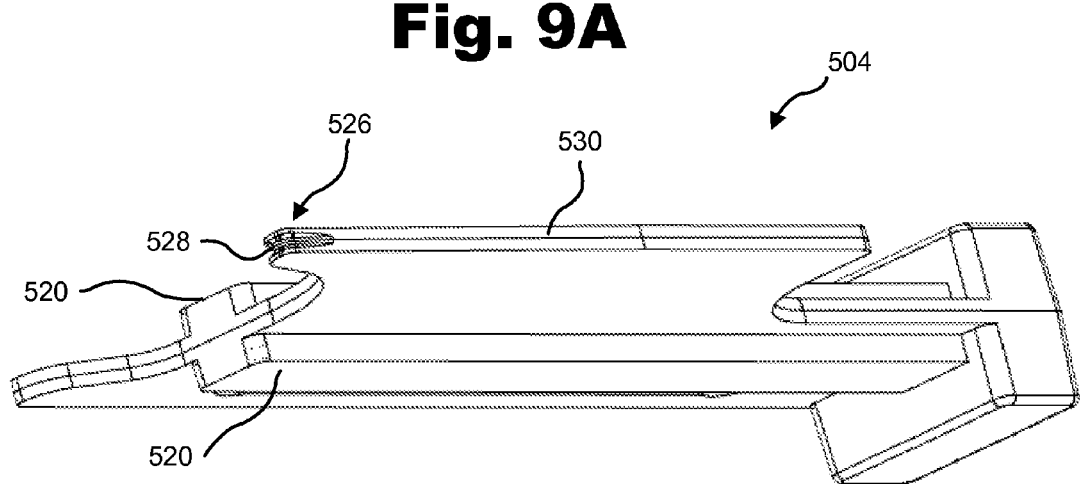
FIG. 9B is a perspective top view of the exemplary slider member of FIG. 9A.

As shown in FIG. 9A, and as shown in further detail in FIG. 9B, which illustrates a perspective top view of slider member 504, slider member 504 may include a straightening edge 526 configured to engage a pre-curved electrode array to move the pre-curved electrode array from a curved configuration to a straightened configuration. Straightening edge 526 may have any size or shape suitable for engaging a pre-curved electrode array. As shown in FIGS. 9A and 9B, straightening edge 526 may comprise a substantially narrow distal tip of slider member 504. In some examples, straightening edge 526 may be configured to engage a pre-curved electrode array without causing damage to the pre-curved electrode array. For example, straightening edge 526 may have a curved or rounded shape (e.g., a bull nose shape) configured to engage and slide along the curved surface of a pre-curved electrode array as slider 504 moves from a first position to a second position to move the pre-curved electrode array from a curved configuration to a straightened configuration without damaging the pre-curved electrode array. Additionally or alternatively, straightening edge 526 may have a groove 528 disposed therein and/or extending around the curvature thereof that is configured to at least partially receive the pre-curved electrode array as straightening edge 526 engages the pre-curved electrode array and/or align the pre-curved electrode array with straightening channel 512. As shown in FIG. 9B, groove 528 may be disposed at least partially along the curved portion of straightening edge 526. In this manner, as shown in FIG. 9B, groove 528 may have a corresponding curved or rounded shape (e.g., a bull nose shape).

Slider member 504 may have an upper surface 530 configured to define at least a portion of straightening channel 512 (e.g., see FIG. 7). Accordingly, straightening edge 526 may engage and straighten a pre-curved electrode array and upper surface 530 may assist in constraining the pre-curved electrode array in a straightened configuration. In further examples, slider member 504 may include any other suitable features for engaging and straightening a pre-curved electrode array.

Loading tool 500 and any component thereof may be made of and/or include any suitable materials. In some examples, loading tool 500 may include one or more plastics (e.g., polymers), metals (e.g., stainless steel), other suitable materials, or combinations thereof. Additionally or alternatively, the materials of loading tool 500 may be substantially transparent to allow a user to see an electrode array within loading tool 500 and verify the position and/or configuration of the electrode array within the loading tool 500. As a result, the user can visually verify that the electrode array is in the proper position and/or configuration prior to straightening the electrode array or inserting a straightening member into the electrode array.

Loading tool 500 is provided for exemplary purposes only. One will appreciate that additional loading tools according to principles described herein may include additional elements or may exclude certain elements disclosed herein.

Figure 10:
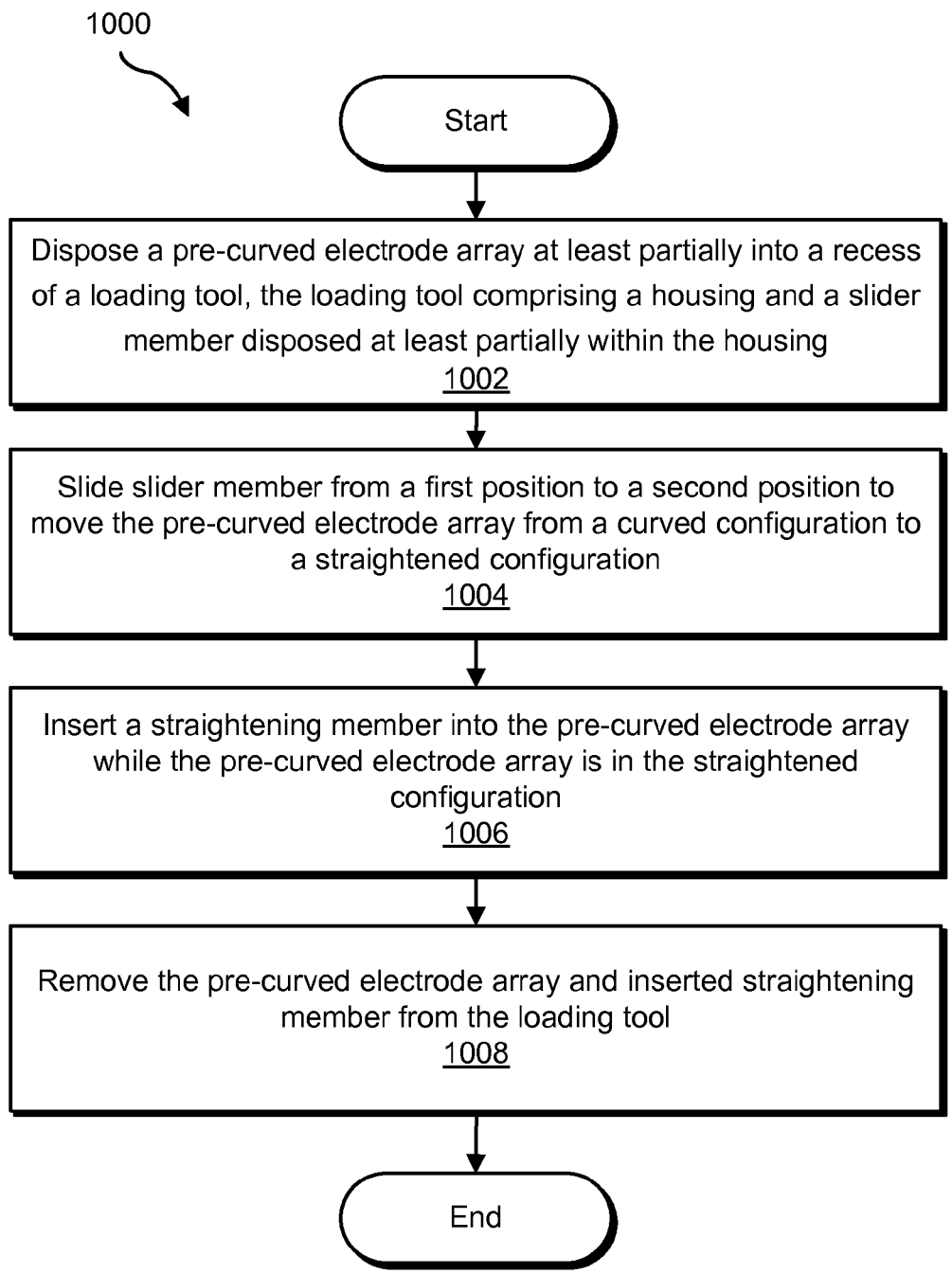
FIG. 10 illustrates an exemplary method of loading a pre-curved electrode array onto a straightening member according to principles described herein.

FIG. 10 illustrates an exemplary method 1000 of loading a pre-curved electrode array onto a straightening member using a loading tool (e.g., loading tool 500) according to principles described herein. While FIG. 10 illustrates exemplary steps according to one embodiment, other embodiments may omit, add to, reorder, and/or modify any of the steps shown in FIG. 10.

In step 1002, a pre-curved electrode array may be disposed at least partially into a loading tool, the loading tool comprising a housing and a slider member disposed at least partially within the housing. In some examples, the slider member may be slidable relative to the housing from a first position to a second position, wherein in the first position the housing and the slider member define a recess configured to receive the pre-curved electrode array in a curved configuration and wherein in the second position the housing and the slider member define a straightening channel configured to constrain the pre-curved electrode array in a straightened configuration. Additionally or alternatively, the slider member may be configured to move the pre-curved electrode array from a curved configuration to a straightened configuration as it slides from the first position to the second position. The loading tool may be similar to any loading tool (e.g., loading tool 500) disclosed herein.

Figure 11A:
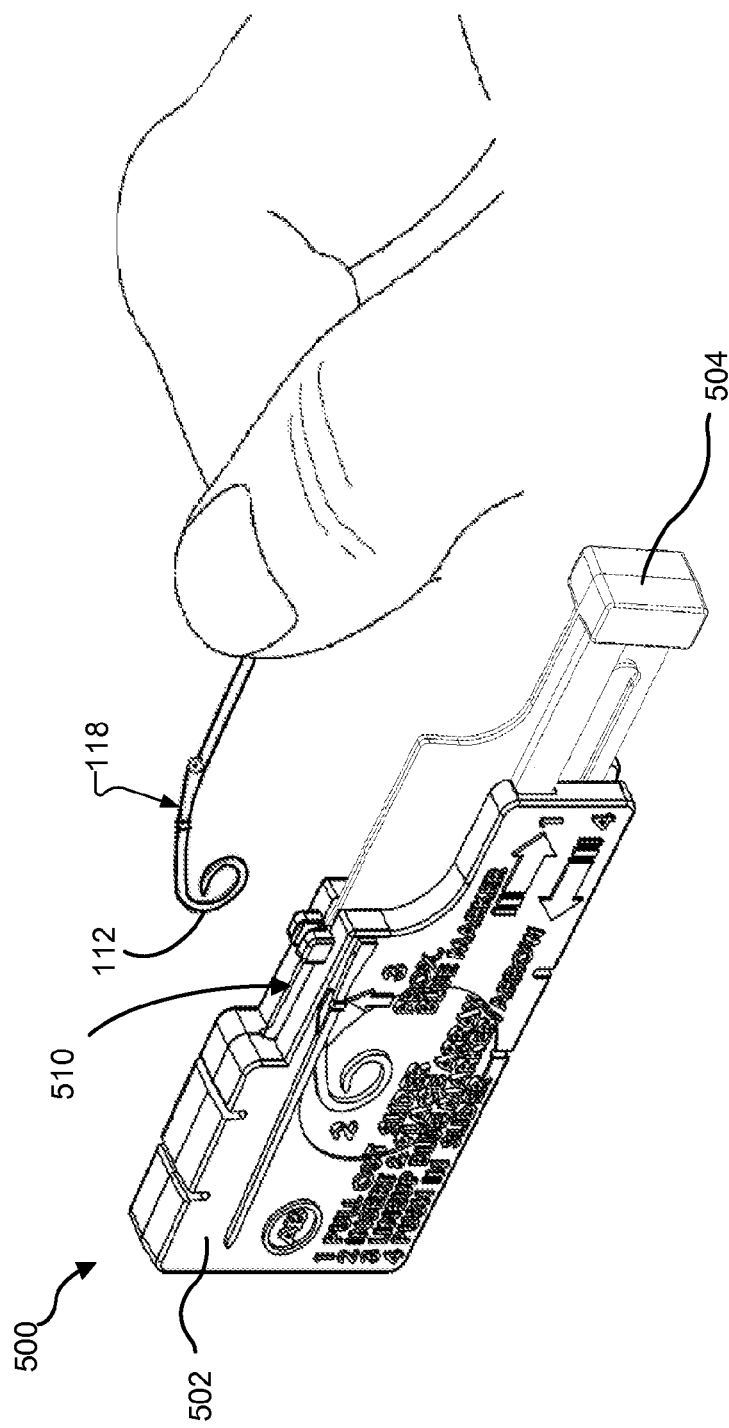
FIG. 11A illustrates a pre-curved electrode array being positioned for use with an exemplary loading tool according to principles described herein.

To illustrate, FIG. 11A shows a lead 118 having a pre-curved electrode array 112 in a curved configuration ready to be disposed at least partially into loading tool 500 with slider member 504 in a first position. As shown, slider member 504 and housing 502 may define recess 510 configured to receive electrode array 112 in the curved configuration. A surgeon or other user may place electrode array 112 within recess 510. FIG. 11B shows electrode array 112 after it has been placed within recess 510. As shown in FIG. 11B, a distal curved portion of electrode array 112 may be disposed at least partially within recess 510 and a portion of the lead 118 proximal of electrode array 112 may be positioned within gripping element 506 (e.g., by pushing the proximal portion of lead 118 down into gripping element 506 in the direction indicated by arrow 1102) to hold electrode array 112 in place.

Figure 11C:
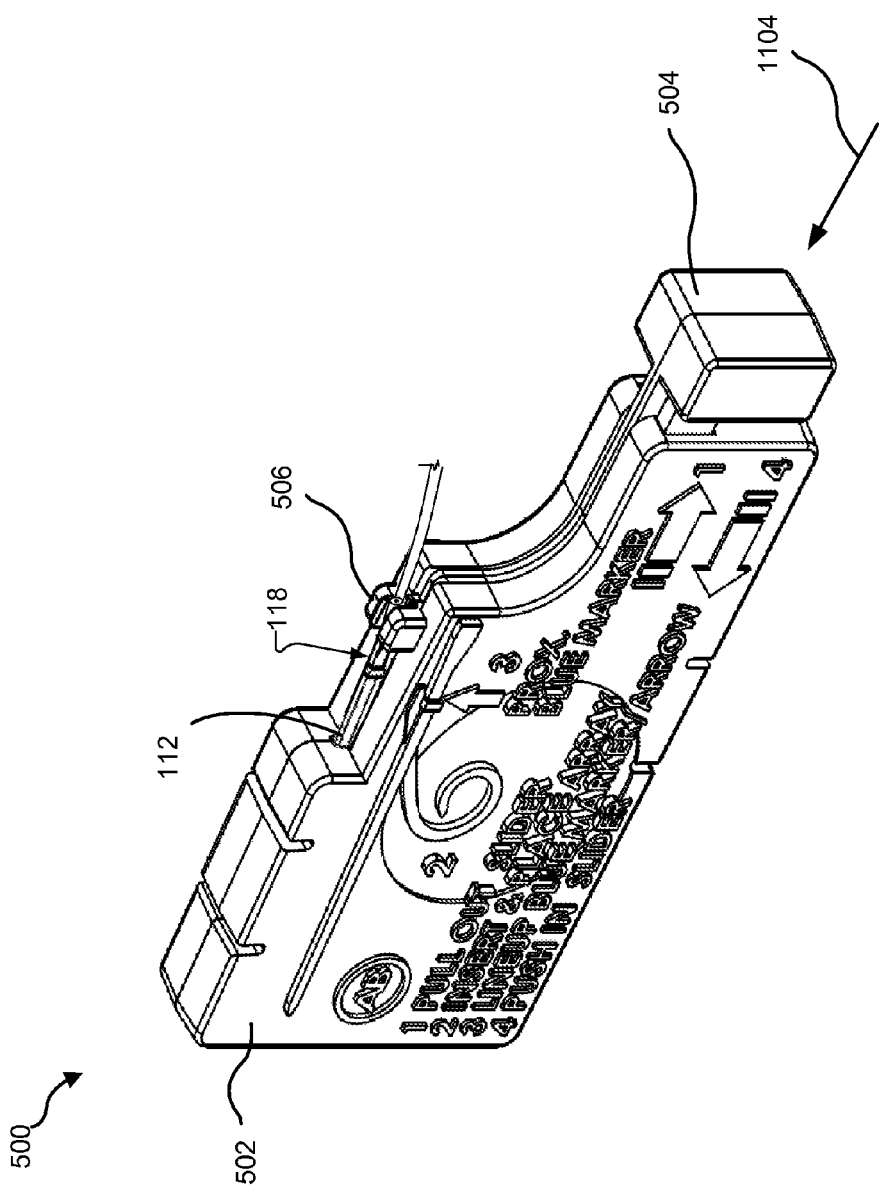
FIG. 11C illustrates a slider member being moved from a first position to a second position to move the pre-curved electrode array from a curved configuration to a straightened configuration according to principles described herein.

In step 1004, the slider member is slid from a first position to a second position to move the pre-curved electrode array from a curved configuration to a straightened configuration. For example, FIG. 11C shows slider member 504 slid to a second position in response to pressure exerted by a user in a direction indicated by arrow 1104. As described in more detail above, as slider member 504 slides from the first position to the second position, slider member 504 may engage electrode array 112 to move electrode array 112 from a curved configuration to a straightened configuration. In certain examples, slider member 504 may move electrode array 112 into a straightening channel (e.g., straightening channel 512 shown in FIG. 7), wherein electrode array 112 may be constrained in the straightened configuration.

Figure 11D:
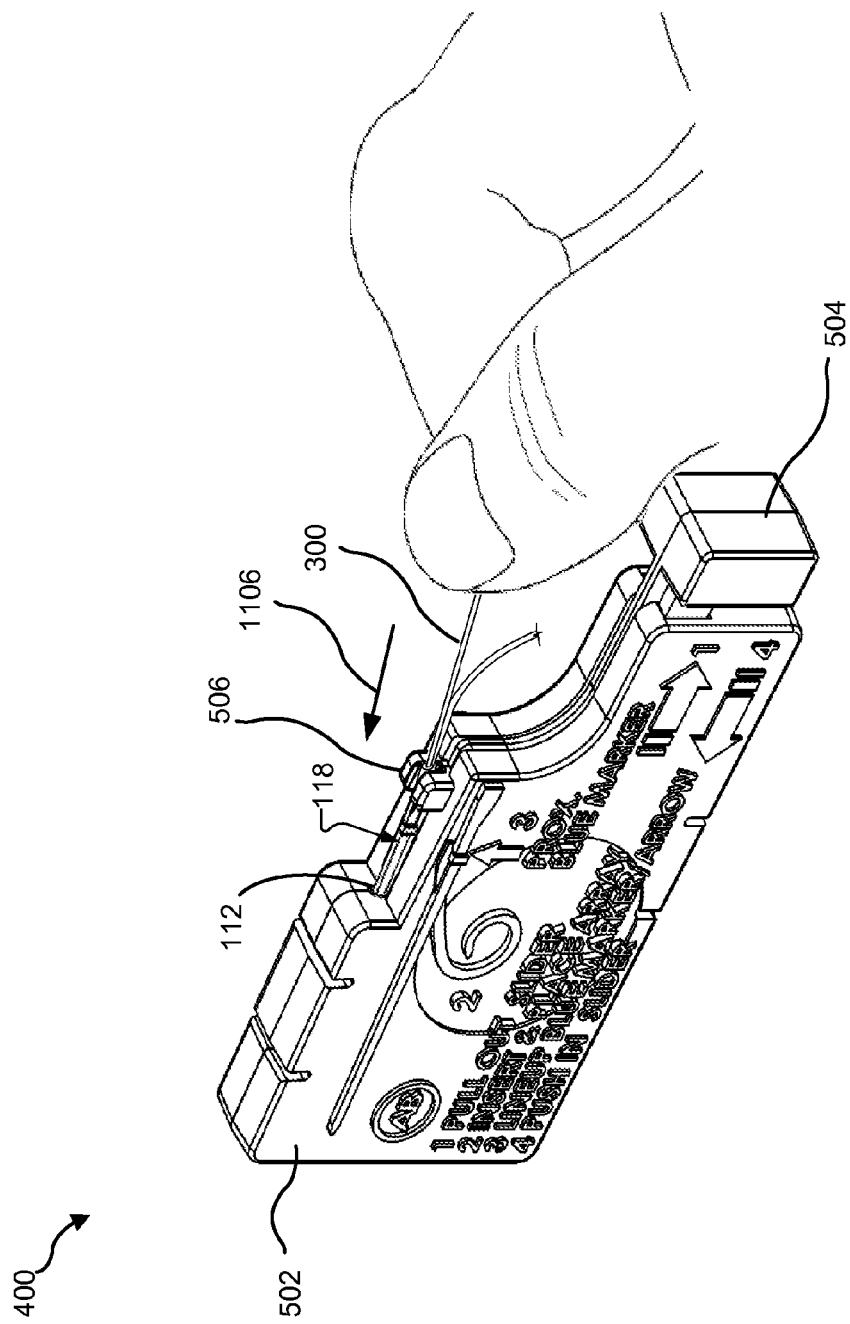
FIG. 11D illustrates a straightening member being inserted into the pre-curved electrode array according to principles described herein.

In step 1006, a straightening member is inserted into the pre-curved electrode array while the electrode array is in the straightened configuration. For example, FIG. 11D shows a straightening member 300 being inserted into electrode array 112 in the direction indicated by arrow 1106 while electrode array 112 is constrained in a straightened configuration within straightening channel 512. By moving the electrode array 112 to the straightened configuration prior to inserting straightening member 300, a user may avoid unnecessarily damaging electrode array 112 during insertion of straightening member 300.

Figure 11E:
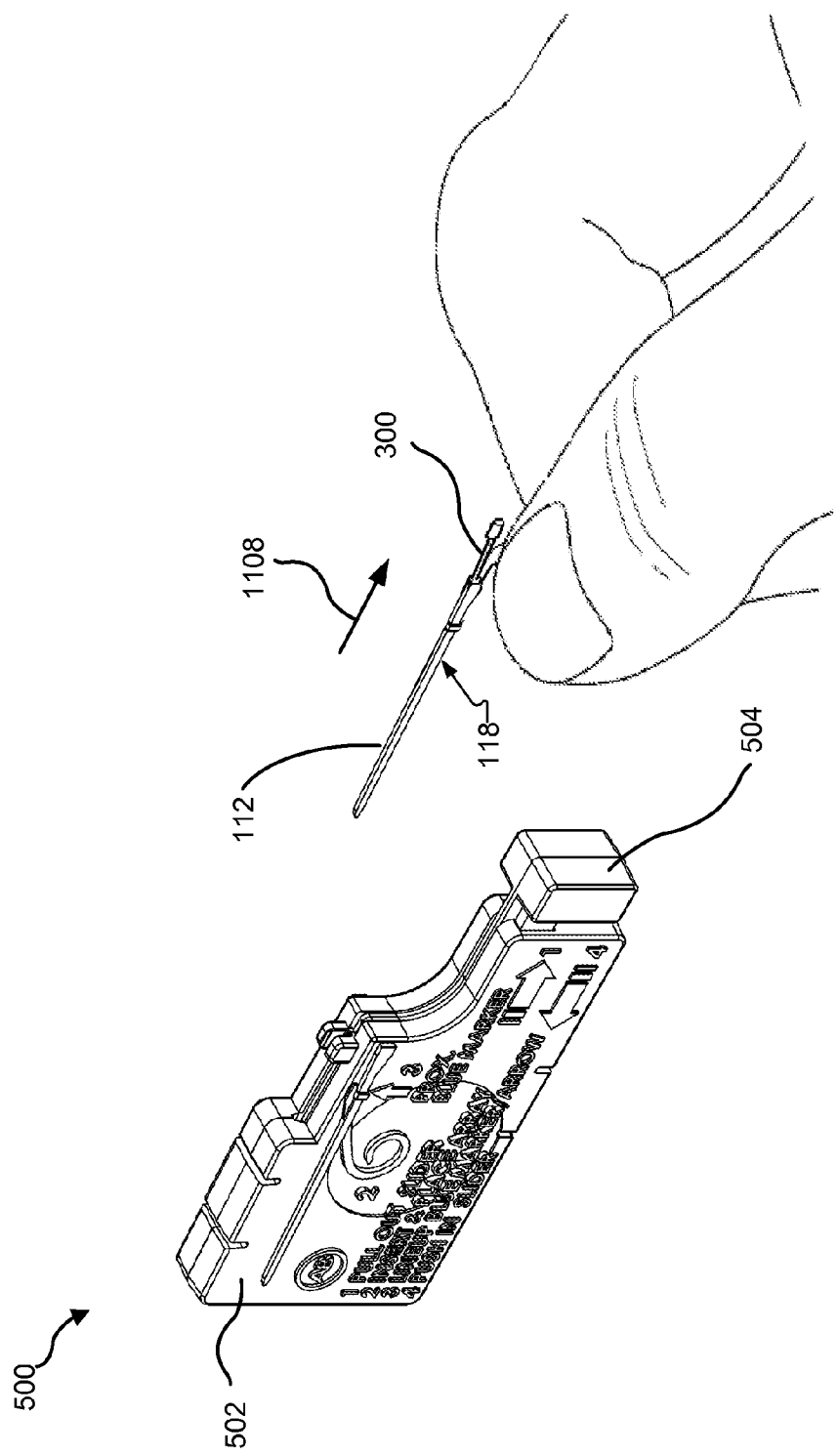
FIG. 11E illustrates the pre-curved electrode array and inserted straightening member being removed from the exemplary loading tool according to principles described herein.

In step 1008, the pre-curved electrode array and inserted straightening member are removed from the loading tool. For example, FIG. 11E shows electrode array 112 and inserted straightening member 300 being removed from loading tool 500. In some examples, electrode array 112 may be pulled in a proximal direction indicated by arrow 1108 out of straightening channel 512. Additionally or alternatively, slider member 504 may be returned to the first position to facilitate removal of electrode array 112 from loading tool 500.

The steps illustrated in FIG. 10 may be performed to initially load a pre-curved electrode array onto a straightening member prior to a medical procedure in which a surgeon or other user attempts to insert the pre-curved electrode array into the cochlea of a patient. The steps illustrated in FIG. 10 may additionally or alternatively be used to reload the pre-curved array onto the straightening member during the medical procedure and/or at any other time as may serve a particular implementation. In this manner, the surgeon or other user may easily reload the pre-curved electrode array onto the straightening member after a failed attempt to insert the pre-curved electrode array into the cochlea.

In some examples, pre-curved electrode array 112 may be inserted into a duct of the cochlea in accordance with an off straightening member insertion technique. As used herein, an "off straightening member insertion technique" comprises any technique used to insert pre-curved electrode array 112 into a duct of the cochlea that, at least during a portion of the insertion process, does not employ the use of an insertion tool coupled to straightening member 300. For example, only the straightening member 300 may be used to initially insert pre-curved electrode array 112 at least partially into the cochlea. At some point, forceps or some other tool may be used to advance the pre-curved electrode array 112 all the way into the cochlea while holding straightening member 300 in a stationary position with respect to the cochlea. It will be recognized that other off straightening member insertion techniques may be used in accordance with the systems and methods described herein. It will also be recognized that any other insertion technique other than an off straightening member insertion technique may be used in accordance with the systems and methods described herein.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system for loading a lead comprising a pre-curved electrode array onto a straightening member, the system comprising:
   a loading tool comprising
      a housing, and
      a slider member disposed at least partially within the housing and slidable relative to the housing from a first position to a second position, wherein in the first position an interior surface of the housing and a portion of the slider member that is disposed within the housing define a recess configured to receive the pre-curved electrode array in a curved configuration, wherein in the second position the interior surface of the housing and the portion of the slider member that is disposed within the housing define a straightening channel configured to constrain the pre-curved electrode array in a straightened configuration, and wherein the slider member is configured to engage the pre-curved electrode array to move the pre-curved electrode array from the curved configuration to the straightened configuration as the slider member slides from the first position to the second position in response to a user pushing the slider member into an interior of the housing; and
   a straightening member configured to be inserted into the pre-curved electrode array while the pre-curved electrode array is in the straightened configuration and retain the pre-curved electrode array in the straightened configuration after the pre-curved electrode array is removed from the loading tool;

wherein the slider member comprises a straightening edge that engages and straightens, as the slider member slides from the first position to the second position, the pre-curved electrode array before the straightening member is inserted into the pre-curved electrode array.

2. The system of claim 1, wherein the straightening edge comprises a groove therein configured to at least partially receive and stabilize the pre-curved electrode array as the slider member slides from the first position to the second position.

3. The system of claim 1, wherein the pre-curved electrode array has a shape that tapers from a proximal end to a distal end and wherein the straightening channel has a tapered configuration corresponding to the tapered shape of the pre-curved electrode array.

4. The system of claim 1, further comprising a gripping element extending from the housing and configured to hold the pre-curved electrode array in place as the slider member slides from the first position to the second position.

5. The system of claim 1, wherein the housing comprises a first side member and a second side member configured to be coupled together.

6. The system of claim 1, wherein the slider member further comprises a guide channel configured to guide the slider member as it slides from the first position to the second position.

7. The system of claim 6, wherein the housing further comprises a guide pin configured to extend through the guide channel of the slider member and guide the slider member as it slides from the first position to the second position.

8. The system of claim 7, wherein the guide channel comprises a first indent configured to receive the guide pin when the slider member is in the first position and resist movement of the slider member from the first position and a second indent configured to receive the guide pin when the slider member is in the second position and resist movement of the slider member from the second position.

9. The system of claim 1, wherein the housing further comprises instructions disposed thereon and configured to direct a user on how to utilize the loading tool, wherein the instructions include at least one of written instructions and graphical indicia.

10. The system of claim 1, further comprising a pre-curved electrode array.

11. The system of claim 1, wherein the housing comprises a substantially transparent material.

12. A method of loading a lead comprising a pre-curved electrode array onto a straightening member, the method comprising:

disposing a pre-curved electrode array at least partially into a loading tool, the loading tool comprising
a housing, and
a slider member disposed at least partially within the housing and slidable relative to the housing from a first position to a second position, wherein in the first position an interior surface of the housing and a portion of the slider member that is disposed within the housing define a recess configured to receive the pre-curved electrode array in a curved configuration, wherein in the second position the interior surface of the housing and the portion of the slider member that is disposed within the housing define a straightening channel configured to constrain the pre-curved electrode array in a straightened configuration, and wherein the slider member is configured to engage the pre-curved electrode array to move the pre-curved electrode array from the curved configuration to the straightened configuration as it slides from the first position to the second position in response to a pushing the slider member into an interior of the housing;

sliding the slider member from the first position to the second position to move the pre-curved electrode array from the curved configuration to the straightened configuration;

inserting, after the pre-curved electrode array has moved from the curved configuration to the straightened configuration, a straightening member at least partially into the pre-curved electrode array while the pre-curved electrode array is in the straightened configuration to retain the pre-curved electrode array in the straightened configuration after the pre-curved electrode array is removed from the loading tool; and removing the pre-curved electrode array and inserted straightening member from the loading tool.

13. The method of claim 12, further comprising positioning a portion of the lead proximal of the pre-curved electrode array into a gripping element extending from the housing to hold the pre-curved electrode array in place as the slider member slides from the first position to the second position.

14. The method of claim 12, wherein the slider member comprises a straightening edge that engages and straightens the pre-curved electrode array as the slider member slides from the first position to the second position, the straightening edge having a curved surface and comprising a groove therein extending at least partially around the straightening edge.

15. A tool for loading a lead comprising a pre-curved electrode array onto a straightening member, the tool comprising:

a housing; and
a slider member disposed at least partially within the housing and slidable relative to the housing from a first position to a second position, wherein in the first position an interior surface of the housing and a portion of the slider member that is disposed within the housing define a recess configured to receive the pre-curved electrode array in a curved configuration, wherein in the second position the interior surface of the housing and the portion of the slider member that is disposed within the housing define a straightening channel configured to constrain the pre-curved electrode array in a straightened configuration, and wherein the slider member is configured to move the pre-curved electrode array from the curved configuration to the straightened configuration as it slides from the first position to the second position in response to a user pushing the slider member into an interior of the housing:

wherein the slider member comprises a straightening edge that engages and straightens, as the slider member slides from the first position to the second position, the pre-curved electrode array before the straightening member is inserted into the pre-curved electrode array.

16. The tool of claim 15, wherein the straightening edge comprises a groove therein configured to at least partially receive and stabilize the pre-curved electrode array as the slider member slides from the first position to the second position.

17. The tool of claim 16, wherein the straightening edge has a curved shape and the groove extends at least partially around the curved shape of the straightening edge.

18. The tool of claim 15, further comprising a gripping element extending from the housing and configured to hold the pre-curved electrode array in place as the slider member slides from the first position to the second position.

19. The tool of claim 15, wherein the slider member further comprises a guide channel and wherein the housing further comprises a guide pin configured to extend through the guide channel, the guide channel and guide pin configured to interact to guide the slider member as it slides from the first position to the second position.

20. The tool of claim 19, wherein the guide channel comprises a first indent configured to receive the guide pin when the slider member is in the first position and resist movement of the slider member from the first position and a second indent configured to receive the guide pin when the slider member is in the second position and resist movement of the slider member from the second position.

* * * * *